United States Patent [19]

Miller et al.

[11] 4,038,148
[45] July 26, 1977

[54] ANAEROBIC ENVIRONMENTAL SYSTEM FOR BACTERIA CULTURE TESTING

[75] Inventors: Lowell Donald Miller, Kansas City, Mo.; Melvin Wayne Hounsell, Beloit, Wis.; Ernest Elliott Spinner, Grandview, Mo.

[73] Assignee: Marion Laboratories, Inc., Kansas City, Mo.

[21] Appl. No.: 643,258

[22] Filed: Dec. 22, 1975

[51] Int. Cl.² ............................ C12B 1/00; C12K 1/10
[52] U.S. Cl. ................................. 195/127; 195/109; 23/282; 195/103.5 M; 195/126
[58] Field of Search ................ 195/127, 109, 126; 23/282, 281

[56] References Cited

U.S. PATENT DOCUMENTS

| 3,246,959 | 4/1966 | Brewer | 195/109 |
|---|---|---|---|
| 3,419,400 | 12/1968 | Hayhurst et al. | 23/282 |
| 3,483,089 | 12/1969 | Brewer | 195/127 |
| 3,655,515 | 4/1972 | Noorlander | 195/127 |

*Primary Examiner*—Alvin E. Tanenholtz
*Attorney, Agent, or Firm*—Merriam, Marshall, Shapiro & Klose

[57] ABSTRACT

A package for storing, incubating or transporting an anaerobic culture comprising a bag of flexible sheet material of low gas permeability, a self-contained gas generating apparatus in the bag for generating at least a reducing gas, a culture retaining container in the bag, and a catalyst in the bag which promotes reaction between the reducing gas, when produced by the gas generating apparatus, and oxygen in the bag. The bag may also contain a color indicator apparatus which when activated indicates the presence or absence of oxygen in the bag by color change. Hydrogen is the preferred reducing gas which is generated, alone or in conjunction with carbon dioxide.

35 Claims, 7 Drawing Figures

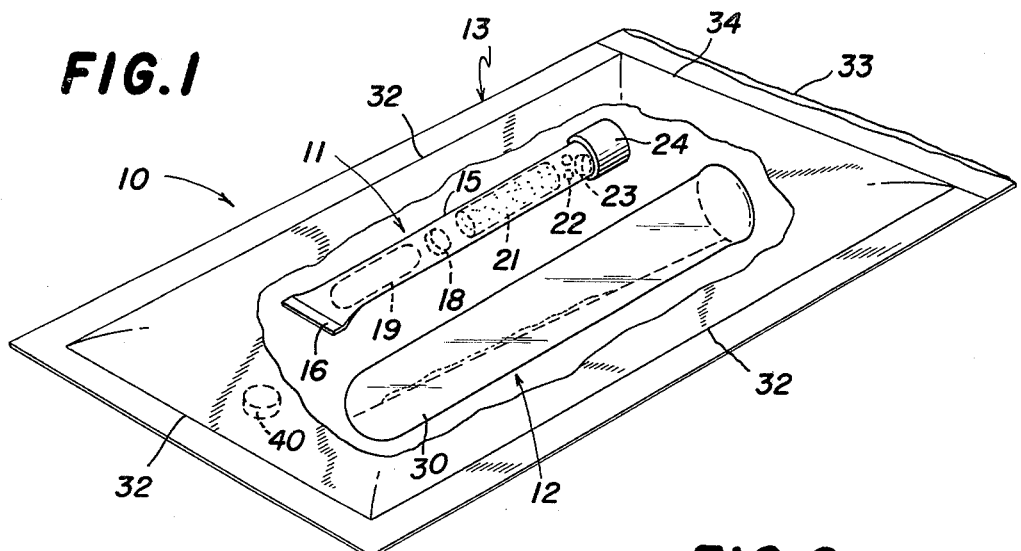
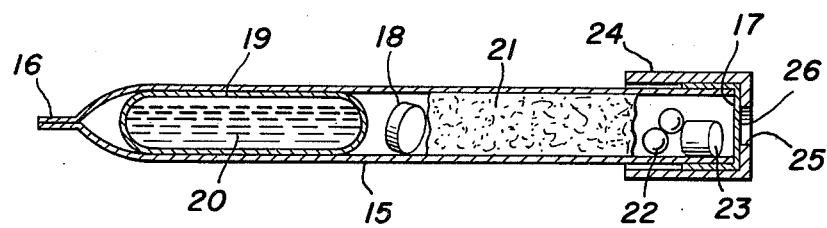
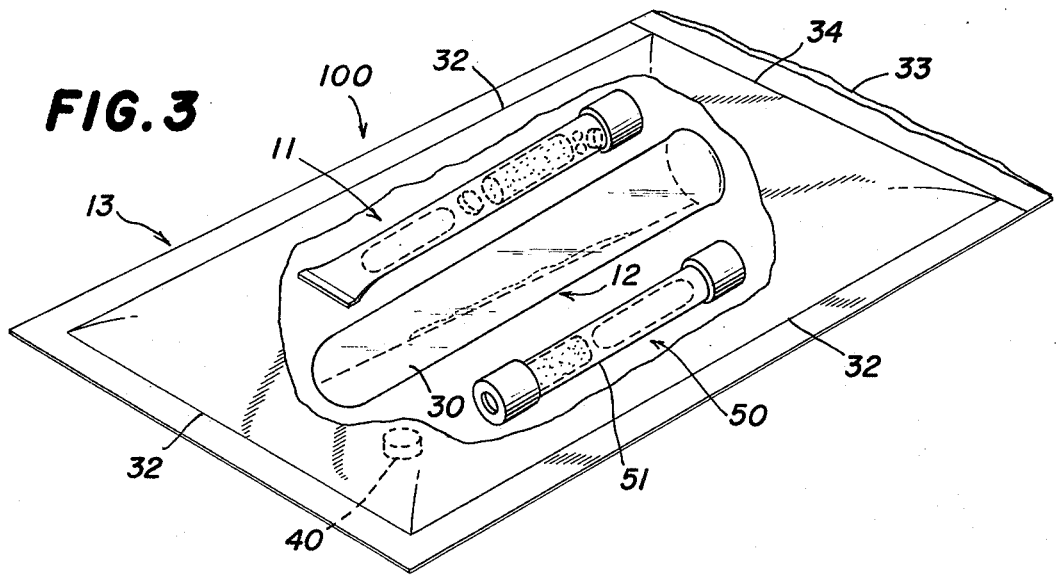
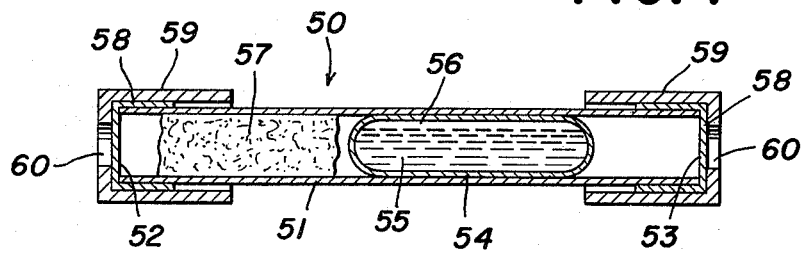

ANAEROBIC ENVIRONMENTAL SYSTEM FOR BACTERIA CULTURE TESTING

This invention relates to apparatus useful in connection with bacteria cultures. More particularly, this invention is concerned with novel packages for storing, transporting and testing anaerobic bacterial cultures, i.e. those of the type which remain viable only when in a gaseous environment or atmosphere low in, or devoid of, oxygen.

Many diseases of man and lower animals are bacterial in origin. The treatment of many bacterial diseases requires that the infecting organism be identified. A drug known to be effective against the infecting organism can then be prescribed.

The identification of an infecting organism is generally by means of a culture obtained from the ill patient or animal. The culture is then transported to a laboratory for determination of the identity of the infecting organism. Such laboratories require highly trained microbiologists and elaborate, expensive equipment. Suitable testing laboratories, accordingly, are not always readily available. It therefore becomes necessary for the patient to visit, or animal be taken to, the laboratory where the culture can be obtained and put immediately into the test procedures or for the culture to be taken at a location remote from the laboratory and then transported to the laboratory for testing.

While the collecting of a culture generally presents no difficulties, the storage and/or transportation of the culture to a testing laboratory under conditions which guarantee the culture will be viable and free of contamination upon arrival presents serious problems. Although contamination from other organisms can generally be avoided by suitable means, the maintenance of a viable culture often requires, in addition to a suitable nutrient medium, the storage and transportation of the culture in a particular gaseous environment which promotes its viability.

Since bacteria of the anaerobic type are known to require an oxygen-deficient or oxygen-free gaseous environment, it is obvious that the transportation of an anaerobic bacteria culture should be effected in an environment having no or little oxygen. Organisms which are obligate anaerobes, such as the bacilli of tetanus, gas-gangrene, botulinus and bacteroides, require the absence of oxygen for proper growth. Although this is generally known by bacteriologists, it is disclosed in Brewer U.S. Pat. No. 3,246,959.

The Brewer U.S. Pat. No. 3,246,959 discloses a gas-producing device for generating an atmosphere conducive for maintaining and increasing the viability of organisms which require a special non-toxic atmosphere. The patent shows the chemical generation of hydrogen, carbon dioxide and acetylene for the purpose of supplying a non-toxic atmosphere to a culture in a container. A platinized wire gauze in the container is heated by electricity for the purpose of completely reacting oxygen in the container.

Anandam U.S. Pat. No. 3,616,263 discloses a culture tube for anaerobic cultures. Oxygen is removed from the tube by use of a divided capsule containing aqueous potassium hydroxide and aqueous pyrogallic acid which when combined form a strong reducing agent for the oxygen.

Although the prior art recognizes the need to maintain various cultures in anaerobic conditions, it has needed a low cost, reliable, disposable package for storage, transport and/or testing of an anaerobic culture.

According to one aspect of the present invention there is provided a package for storing, incubating or transporting an anaerobic culture comprising an open or closed bag of flexible transparent sheet material of low gas permeability, a self-contained gas generator apparatus in the bag for generating at least a reducing gas, a culture retaining container in the bag, and a catalyst in the bag which promotes reaction between the reducing gas, when produced by the gas generator apparatus, and oxygen in the bag. It is furthermore advisable to include in the bag a color indicator apparatus which when activated indicates the presence or absence of oxygen in the bag by color change.

According to a further aspect of the invention a self-contained gas generator apparatus and a color indicator apparatus are included in an open or closed bag of flexible transparent sheet material of low gas permeability but no culture retaining container is included in the bag since such a container may preferably be obtained from some other available source.

The reducing gas produced by the gas generator will generally be hydrogen, although it can be some other reducing gas readily produced chemically, such as acetylene. Furthermore, in addition to the production of a reducing gas the gas generator may simultaneously produce carbon dioxide since at least some anaerobic bacteria are maintained more viable in the presence of higher amounts of carbon dioxide than are normally present in air.

When a culture retaining container is included in the bag it may take any suitable form for holding and supporting a culture. Furthermore, the container may be devoid of a suitable nutrient media or a nutrient media may be included with the container. Suitable types of containers for the culture are the conventional media plate or petri dish, a media tube such as of the test tube type with or without a cap or a media strip having a series of microtubes which contain different media so that the identification of the culture may be determined by comparison with predetermined color standards for each of the microtubes. A commercially available media strip is identified as the API 20 anaerobe system (Analytab Products, Inc., Plainview, N.Y.).

Since it is desirable to activate the gas generator after a culture has been placed in the bag and the bag has been subsequently sealed shut, the self-contained gas generator should be one which is readily activated from outside the bag. Such a gas generator may include an ampoule which contains a liquid which is reactive with a solid gas-producing material. Upon rupture of the ampoule by the application of force through the bag the liquid may be released to produce the desired chemical reaction to generate the desired reducing gas in a volume which is adequate to combine with all of the oxygen present in the air in the closed bag but less gas than would cause the bag to rupture from the gas pressure.

The color indicator used in the various packages provided by this invention is also advisably self-contained and comprises a container which permits flow of gas thereto, an ampoule in the container containing a redox color indicator liquid, and an absorbent material positioned to absorb the liquid when it is released from the ampoule. The color indicator is advisably one which can be activated when the bag is closed by the application of pressure through the bag against the ampoule walls. Such activation is readily achieved by using a container for the color indicator in the form of a flexible polymeric tube or a bag. When the container is a tube, the ampoule may be positioned snugly in the tube but when it is crushed and the redox liquid is freed to be absorbed on a fibrous plug positioned therein the interior space of the tube is opened so that flow of gas through the tube is permitted. The ampoule may also be covered by a non-woven sheet of polyester fibrous material surrounded by a bag-like covering of knitted synthetic material.

The described anaerobic culture packages are readily produced at low cost. All of the components employed in the packages are intended to be of the disposable type which are used once and then discarded. All of the components employed in the packages are readily sterilized such as by ethylene oxide gas. The gas generating apparatus and the color indicator apparatus may be placed in the bag, with or without a culture retaining container, and sterilized with the bag mouth open. The bag mouth may then be left open or it may be closed, such as by a heat seal. Each form has commercial uses.

The presence of the gas generator in the package makes it unnecessary for other means to be used to create the desired anaerobic atmosphere. Furthermore, the presence of the color indicator permits the technician to determine within a short time after the gas generator is activated if the desired anaerobic atmosphere is produced. Also, since the color indicator is intended to stay with the package while it is transported, and even during test procedures which may be conducted without opening the bag, one is able to determine at any time whether the anaerobic atmosphere has been maintained and exists at the time of observation.

The invention will be described further in conjunction with the attached drawings, in which:

FIG. 1 is a perspective view of a package for transporting an anaerobic bacteria culture and contains a gas generating apparatus and a culture retaining container in a flexible bag;

FIG. 2 is a longitudinal, axial sectional view of the gas generating apparatus shown in the package of FIG. 1;

FIG. 3 is a view of a package such as shown in FIG. 1 but with a color indicator apparatus also included therein;

FIG. 4 is a longitudinal, axial sectional view of the color indicator apparatus shown in the package of FIG. 3;

So far as is practical the same elements or parts which appear in the various views of the drawings will be identified by the same numbers.

Figure 5:
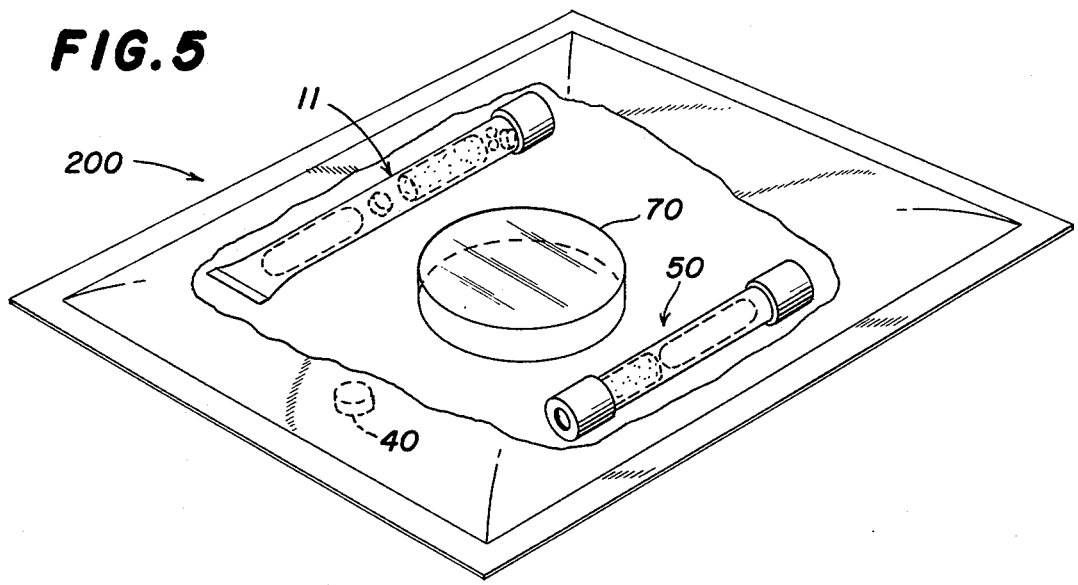
FIG. 5 is a perspective view of a package provided according to the invention containing a gas generating apparatus, a color indicator apparatus and a media plate in a flexible bag.

With reference to FIG. 1, the bacteria culture storing and transporting package 10 constitutes a gas generating appartus 11 and a media tube 12 both placed inside of flexible transparent bag 13.

The gas generating apparatus 11 comprises a container in the form of an elongated plastic tube 15 (FIGS. 1 and 2) which is closed at end 16 and is open at end 17.

The tube 15 may be made of a flexible but self-supporting polymeric material such as polyethylene, polypropylene or a polyethylene-polypropylene copolymer such as the one available as Avisun 6011.

One or more gas generating solid tablets or pellets 18 is positioned in tube 15 above the ampoule 19. The tablet 18 has a composition which is suitable for generating a reducing gas such as hydrogen or acetylene, or both a reducing gas and carbon dioxide.

Ampoule 19 is positioned in tube 15 more or less snugly so that it maintains its position. A liquid 20 is contained in ampoule 19. The composition of liquid 20 is selected so that it, when released from ampoule 19, will react with tablet 18, which drops into the liquid, to generate one or more gases. The ampoule 19 can be made of glass or some other material which is nonreactive with liquid 20 or the components of gas generating tablet 18. The ampoule 19 is advisably made so that it will rupture or break upon application of finger pressure to the outside of tube 15 adjacent the ampoule wall. In this way the ampoule may be opened and the liquid 20 freed to react with tablet 18.

A liquid absorbent plug 21, such as of polyester fibers, is positioned in tube 15 after the ampoule 19 and tablet 18 are placed in the tube. The absorbent plug 21 is thus located between the ampoule 19 and the tube open end 17 so that liquid cannot flow from the tube.

One or more desiccant pellets 22 are advisably positioned between liquid absorbent plug 21 and the open end 17 of the tube 15 as shown in FIG. 2. Any suitable desiccant or water dehydrating material can be used for this purpose although it is preferred to use molecular sieves. Nevertheless, magnesium sulfate or calcium chloride are representative of other desiccant materials which may be used satisfactorily.

Also positioned between liquid absorbent plug 21 and the open end 17 of tube 15 is at least one catalyst pellet 23. The catalyst pellet 23 is provided to induce catalytic reaction between the reducing gas which is formed by the reaction of liquid 20 with tablet 18 and any oxygen which may be in tube 15 and bag 13. A 5% palladium-on-alumina catalyst may be used when hydrogen is the reducing gas although other catalysts which induce the reaction at room temperature may be employed.

A polymeric cap 24 having a central hole 25 and a fibrous biological filter 26 is pressed firmly over the open end of tube 15. The filter 26 is made of a material which will permit gas generated in tube 15 to flow from the tube readily but which will remove any bacteria which may be possibly present in tube 15 and which might otherwise escape during the flow of gas from the tube.

The gas generating tablet 18 may have the following composition when it is desired to produce simultaneously both carbon dioxide and hydrogen as the reducing gas:

Potassium borohydride: 78 mg.
Zinc: 78 mg.
Sodium chloride: 90 mg.
Sodium bicarbonate: 84 mg.
Lactose DT: 164 mg.
Microporous cellulose—Avicel PH 102: 150 mg.
Tabletting lubricant—Calcium stearate: 6 mg.

If it is desired to produce only hydrogen and no carbon dioxide the sodium bicarbonate may be omitted from the composition set forth above for tablet 18.

The ampoule 19 may contain as the liquid 20, 1.1 ml. of 1.8 N hydrochloric acid in a glass ampoule 1 13/16 inches long. It should be understood, however, that the size of ampoule 19 and the strength and quantity of liquid 20 in the ampoule are coordinated with the ingredients of tablet 18 so as to result in the generation of a predetermined volume of one or more gases which will fill bag 13 when closed without developing a gas pressure which will cause it to rupture.

The dehydrating agent or desiccant 22 is advisably included in the gas generating apparatus to remove water and water vapor therefrom which may enter the tube through opening 17 during sterilization, such as by ethylene oxide gas sterilization, in the manufacturing process, or to remove water vapor which may penetrate the tube in one way or another. Removal of water in this way is desirable to preserve the stability of the gas generating tablet 18, although it is understood that under some conditions the desiccant may not be necessarily employed.

The described gas generating apparatus 11 constitutes a disposable throw-away unit which is intended to be employed only once for the production of a reducing gas alone or with carbon dixoide. It is particularly useful in culture collecting and transporting systems where it is considered advisable for an organism to remain viable to be surrounded by an oxygen-free or low oxygen atmosphere. The gas generating apparatus is also highly useful for generating a carbon dioxide atmosphere for use in transporting or storing bacteria cultures which require, or are most likely to remain viable longer, when placed in an atmosphere containing a substantial amount more of carbon dioxide than is found in the atmosphere. Since certain micro-organisms require an atmosphere both enriched with carbon dioxide and substantially oxygen-free the gas generating apparatus provided herewith is particularly useful in conjunction with transporting a culture of these organisms.

The bag 13 shown in FIG. 1 may be made of transparent polymeric flexible film or sheet material of low gas permeability. The bag 13 may be made of two sheets of plastic film heat sealed 32 around three-side edges, thereby leaving an open mouth 33 through which the media tube 12 and the gas generating apparatus 11 are inserted. Specifically, a polyester (Mylar) laminate identified as No. CL5040 (Clear Lam Products) or Scotch Pak No. 48 may be used for the bag. The mouth 33 may be left open or be sealed shut in any suitable way, such as by means of heat seal 34.

The media tube 12 is shown in FIG. 1 containing agar slant 30; however, it is also contemplated that the media tube may be included empty and any suitable nutrient media added by the user of the package. In addition, instead of media tube 12, a media plate with or without a nutrient media or a media strip, may be substituted for it in the package.

The anaerobic culture package shown in FIG. 1 may be employed by opening the bag 13 at heat seal 34 to remove media tube 12. A culture may then be applied to agar slant 30. The innoculated media tube 12 is then replaced in bag 13 and closed such as by a heat seal similar to heat seal 34. Alternatively, the open mouth or end of the bag may be folded or rolled tightly on itself and the folded portion secured in place by a suitable clip or fastener. The resulting package is then put in vertical position with the cap 24 of the gas generator 11 in top position. The ampoule 19 is then broken by squeezing tube 15. The acid in the ampoule 19 is thereby released and tablet 18 drops into the liquid. Reaction of the acid with the potassium borohydride causes hydrogen to be generated within the tube while reaction of the acid with the sodium bicarbonate results in the generation of carbon dioxide. Both of these gases flow through the entire length of tube 15 since plug 21 is gas permeable. Plug 21 absorbs excess acid and prevents it from flowing elsewhere in the tube. The liquid acid also combines with the ingredients of tablet 18 to form a slush which further serves to hold the liquid acid in place. The hydrogen intermixes with the oxygen in tube 15 and by means of the catalyst 23 these two gases react to form water, thereby scavenging oxygen from the internal space of tube 15. Oxygen from bag 13 also flows into tube 15 and is caused to react with the hydrogen by means of the catalyst 23.

As the hydrogen and carbon dioxide are generated in tube 15 the gases flow out opening 17 through filter 26 into bag 13 which, if desired, may contain at least one catalyst pellet 40 like catalyst pellet 23. When catalyst pellet 40 is to be used it is unnecessary, even though advisable, to include the catalyst pellet 23 in the tube 15. The generated gases cause the bag 13 to balloon or expand outwardly. The ballooning effect is evidence that the gases have generated as expected. However, immediately upon generation of hydrogen one or both of the catalyst pellets 23 and 40 induces reaction of the hydrogen with the oxygen to form water. The described catalytic removal or oyxgen from bag 13 does not significantly effect the ballooning immediately. However, about 48 hours or so after the unit is activated the carbon dioxide may have penetrated the walls of bag 13 causing a vacuum to develop therein. The external atmospheric pressure may then press or collapse the flexible walls of the bag together. This condition may result even without oxygen entering the bag because the gas permeability of the wall material may permit preferential flow of carbon dioxide and nitrogen out of the bag but not oxygen in.

Although the above example illustrates the production of hydrogen as the reducing gas by the use of specific chemicals, i.e. potassium borohydride, zinc, sodium chloride and dilute hydrochloric acid, other solid materials can be used in conjunction with other liquids to produce hydrogen or some other reducing gas which will react catalytically with oxygen to remove it from the space around the culture. Thus, water alone can be placed in ampoule 19 and the solid pellet 18 can be formulated to contain a material which reacts with water safely and reasonably quickly to produce hydrogen. Thus, sodium borohydride, lithium aluminum hydride, lithium hydride, calcium hydride, aluminum hydride and lithium borohydride can be used since they react with water as well as aqueous acid to form hydrogen. Such hydrides also react with other liquids such as alcohols to form hydrogen so that sometimes it may be desirable to replace the water or acid with an alcohol, provided it does not adversely affect the culture. Hydrogen can, of course, be produced by the reaction of a metal such as iron, zinc, aluminum and magnesium with a suitable acid such as sulfuric acid and hydrochloric acid.

Instead of using hydrogen as the reducing gas to remove oxygen from the tube 15, it is feasible to form acetylene by the reaction of calcium carbide in pellet 18 and water or dilute acid in ampoule 19.

The chemical means suitable for generating the gaseous carbon dioxide in the apparatus of this invention is not to be limited to the specific embodiment set forth herein. Other well known chemical means for gaseous carbon dioxide generation may be used. Broadly, any solid material which upon contact with a liquid releases carbon dioxide in adequate amount in a reasonably short time may be used. The least expensive method, of course, is to contact a carbonate or bicarbonate salt with a dilute acid which will not produce vapors having an adverse effect on the culture. Instead of putting a dilute acid in the ampoule it can be filled with water, and sodium bicarbonate and citric acid, or some suitable acid salt, can be put in pellet 18 to generate carbon dioxide. Other feasible systems will appear readily to skilled chemists.

FIG. 3 illustrates an anaerobic package 100 like that shown in FIG. 1 but with a color indicator apparatus 50 also included in the bag 13 for determining the presence of oxygen. The color indicator apparatus comprises an open container which permits flow of gas therethrough, an ampoule in the container with the ampoule containing a redox color indicator liquid, and an absorbent material in the container. It is intended that when the liquid is released from the ampoule it be taken up by the absorbent material rather than to have the liquid flow freely in the container. Although any suitable form of container can be used for the color indicator, it is advisable that it be in the form of a tube which is open at both ends. By dimensioning the ampoule to fit snugly in the tube, the ampoule may be opened by rupturing or breaking it by means of finger pressure applied through bag 13 to the external surface of the tube adjacent the ampoule. The liquid redox color indicator so released from the ampoule may then be caused to flow onto an absorbent fibrous plug also fit snugly in the tube. The liquid is absorbed in this way and held in place so as to provide a relatively easily seen mass which can be observed through the transparent wall of the tube. By making the absorbent plug of a white fibrous material the color of the redox liquid indicator can be readily observed and the presence or absence of oxygen thereby determined.

The color indicator apparatus 50 shown in FIGS. 3 and 4 has an elongated flexible transparent tube 51 which is open at its ends 52 and 53. Tube 51 may be made of any suitable material although a flexible polymeric material such as polyethylene is particularly suitable for the tube. Ampoule 54 is snugly positioned within tube 51. The ampoule 54 may be made of any suitable material but desirably is made of relatively thin glass so that it can be easily opened by fracturing the ampoule walls by applying finger pressure through bag 13 against the adjacent surface of tube 51.

The ampoule 54 contains a liquid redox color indicator 55 which occupies most if not all of the space in the ampoule. The ampoule 54 shown in FIGS. 3 and 4 contains an appropriate quantity of liquid and has a top space 56 filled with an inert gas such as nitrogen.

A fibrous liquid absorbent plug 57 is snugly positioned in tube 51 below ampoule 54. The fibrous plug 57 is made of a material which is nonreactive with the redox liquid such as polyester fibers or some other such liquid absorbent material.

It is considered advisable to cover each end of tube 51 with a bacteriological filter 58 through which microorganisms will not pass. In this way, any organisms in tube 51 are prevented from escaping to contaminate the surrounding environment. Each filter 58 is gas permeable but is also, desirably, one which is permeable to liquid, particularly water. The filter 58 at each end of the tube is held in place by a cap 59 having a hole 60 in the top portion.

The redox color indicator liquid 55 may be selected from any suitable material which will change color when the atmosphere around it changes from one which is oxygen deficient to one where there is a significant or substantial amount of oxygen in the atmosphere. Thus, the indicator may have one color in the presence of oxygen and a different color in an atmosphere which is devoid of oxygen. Also, the indicator may be colorless when no oxygen is present and develop a color when oxygen is present, or the indicator may be colorless when oxygen is present and develop a color when little or no oxygen is present in the surrounding atmosphere.

A particularly useful redox color indicator is resazurin in water. This redox indicator is colorless in an atmosphere devoid of oxygen but in an oxygen-containing atmosphere it has a pink color. When this indicator is used it is advisable to include a small amount of cysteine hydrochloride with it since this ingredient facilitates color change. Another specific redox color indicator which may be used is methylene blue. This indicator is colorless in the absence of oxygen but in oxygen, such as in the presence of air, it has a blue color. It is furthermore desirable that the redox color indicator used be one which is color reversible so that any change from an oxygen-containing atmosphere to an atmosphere devoid of oxygen, or from an atmosphere devoid of oxygen to one containing oxygen, will be indicated by the color change.

The preferred redox color indicator for use in the apparatus is aqueous resazurin containing cysteine. A 0.001% solution of resazurin in water is specifically useful.

The anaerobic culture package shown in FIG. 3 may be used by opening closed bag 13. A culture is then deposited on agar slant 30 in media tube 12 and the innoculated tube is then replaced in bag 13. Bag 13 is then closed by a heat seal or repeated folding to make it substantially gas tight. With bag 13 positioned vertically, and with the color indicator apparatus 50 also vertically located, the tube 51 is squeezed adjacent ampoule 54 to crush the ampoule and release the color indicator liquid 55 permitting it to flow downwardly to be absorbed on fibrous plug 57. Since bag 13 contains air the plug 57 will quickly develop a pink color when the indicator liquid is resazurin. The interior space of bag 13 is then filled by gas generated by activating gas generating apparatus 11. The hydrogen which is generated reacts catalytically with oxygen in the bag to produce water and thereby develop an anaerobic atmosphere in the bag. The decrease in oxygen concentration in the bag is evidenced by the pink color of the plug 57 changing to light pink and finally to the white color of the plug when made of polyester fibers, indicating the oxygen has been removed. If oxygen subsequently leaks into bag 13 the plug 57 will redevelop a pink color since the color change is reversible when resazurin is used as the color indicator.

FIG. 5 illustrates a further embodiment of the invention and shows an anaerobic culture package 200 like that of FIG. 3 but with the media tube 12 of FIG. 3 replaced by a media plate 70. The media plate 70 may be empty or prefilled with a nutrient base, such as agar. The package 200 of FIG. 5 is intended to be used in the same way as the package of FIG. 3.

Figure 6:
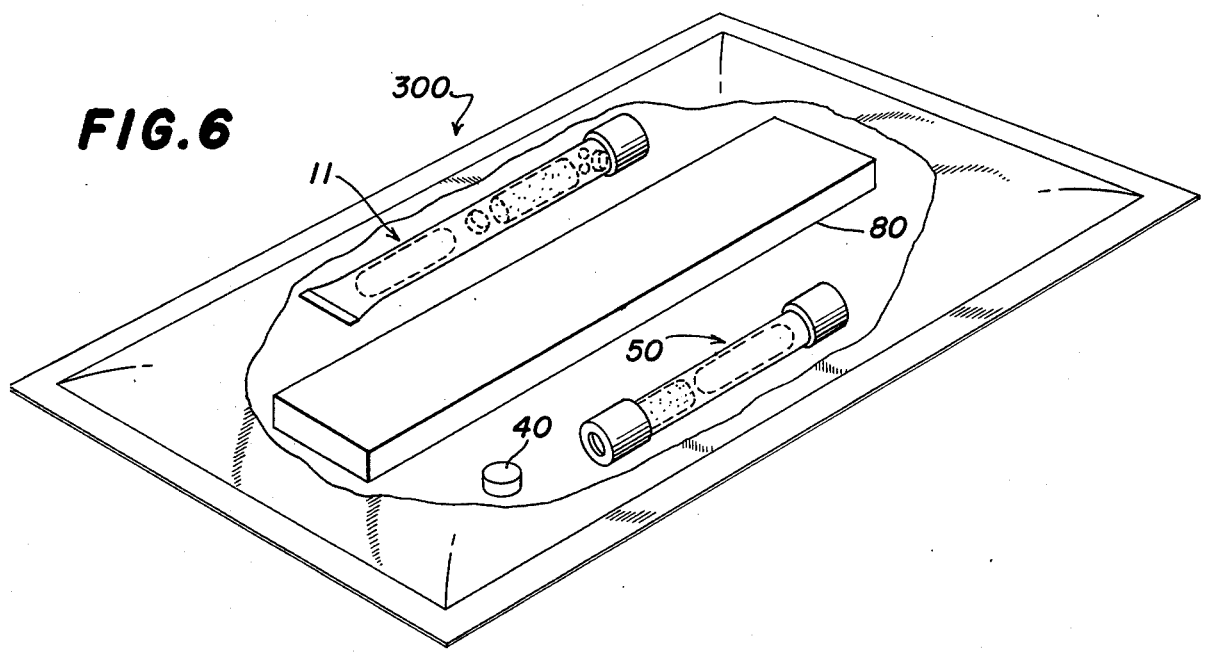
FIG. 6 is a perspective view of another form of package provided by the invention which contains a gas generating apparatus, a color indicator apparatus and a media strip positioned in a flexible bag.

A further embodiment of the invention is shown in FIG. 6. The anaerobic culture package 300 of FIG. 6 has a media strip 80, containing a plurality of microtubes for use in identifying a sample unknown culture, in place of the media plate 70 in the package 200 of FIG. 5 of the media tube 12 in the package 100 of FIG. 3. The media strip 80 may be of any suitable type but desirably is of the type marketed under the name API 20 Anaerobe System (Analytab Products Inc., Plainview, N.Y.) which allows rapid and reliable simultaneous performance of more than 20 biochemical tests for the identification of anaerobic bacteria conveniently and economically. The media strip 80 may be included in the package 300 as manufactured or it may be obtained separately and placed in bag 13 after being innoculated. In that case, the package 300 will comprise the bag 13, gas generating apparatus 11 and color indicating apparatus 50. Regardless of the source of the media strip, the package 300 is employed by placing an innoculated media strip in bag 13 containing the gas generating apparatus 11 and color indicating apparatus 50. The bag 13 is then sealed gas tight. The color indicating apparatus and the gas generating apparatus are then activated. An anaerobic atmosphere, with or without generated carbon dioxide, is created in bag 13 as described previously. The bag and contents may then be incubated at 37° C. The nature of the package permits examination of bacterial growth without disturbing the anaerobic environment. Also, the color indicator constantly shows if oxygen is present or not in the bag. An added advantage of the described package is that it can be discarded without opening the bag thereby aiding in maintaining non-contaminated conditions.

Figure 7:
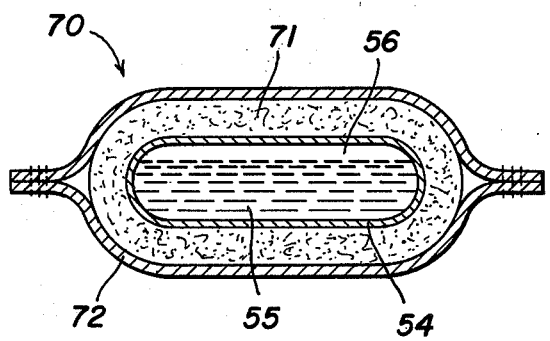
FIG. 7 is a sectional view of a second embodiment of color indicator apparatus which may be used in the invention.

FIG. 7 shows another color indicator apparatus 70 which can be used in the invention in place of color indicator apparatus 50. Color indicator apparatus 70 has ampoule 54 surrounded by a pad-like layer 71, such as of polyester fibers, which in turn is covered or surrounded by a knitted bag 72 made from a knitted tube joined together at both ends. Ampoule 54 is readily fractured by pressing on bag 72. The released color indicator liquid is absorbed on layer 71 and indicates the presence of oxygen, or lack thereof, by its color as herein previously described.

As previously indicated, the invention provides packages comprising a bag having a gas generating apparatus and a color indicator apparatus therein. Such a package is a highly useful article of commerce even if no culture deposit means is subsequently placed in the bag because the combination of gas generator and color indicator can be used with other prior art devices employed in handling, storing, transporting and testing anaerobic cultures.

The foregoing detailed description has been given for clearness of understanding only, and no unnecessary limitations should be understood therefrom, as modifications will be obvious to those skilled in the art.

What is claimed is:

1. A package for storing and transporting an anaerobic culture comprising:
   a bag of flexible sheet material of low gas permeability;
   a self-contained gas generating apparatus in the bag for generating at least a reducing gas;
   a culture retaining receptacle in the bag; and
   a catalyst in the bag which promotes reaction between the reducing gas, when produced by the gas generating apparatus, and oxygen in the bag;
   said gas generating apparatus comprising a container having an opening, a reducing gas generating solid material in the container, an ampoule containing a liquid which is reactive with the solid material to produce a reducing gas catalytically reactive with oxygen at room temperature, said ampoule being openable from outside the container to free the liquid to contact the solid material, and means in the container which prevents liquid from flowing from the container after the ampoule is opened but which permits flow of reducing gas generated in the container out of the opening.

2. A package according to claim 1 in which the bag contains a color indicator apparatus which when activated indicates the presence or absence of oxygen in the bag by color change.

3. A package according to claim 1 in which the gas generating apparatus also produces carbon dioxide.

4. A package according to claim 1 in which the culture retaining receptacle is a media plate, media tube or media strip having a series of microtubes containing different media.

5. A package according to claim 1 in which the reducing gas is hydrogen.

6. A package according to claim 1 in which the container of the gas generating apparatus has a solid desiccant material therein which absorbs water which may enter the container before the ampoule is opened, thereby preventing degradation or premature reaction of the gas generating solid material.

7. A package according to claim 5 in which the gas generating apparatus container contains a catalyst which induces reaction of the generated hydrogen with oxygen in the air to produce water.

8. A package according to claim 5 in which the solid material also produces carbon dioxide.

9. A package according to claim 1 in which the liquid in the ampoule is water or aqueous acid and the gas generating solid material is reactive therewith to produce a reducing gas.

10. A package according to claim 1 in which the gas generating apparatus container opening is covered by a microbacteriological filter.

11. A package according to claim 1 in which the gas generating apparatus container is an elongated flexible tube having an opening at one end.

12. A package according to claim 11 in which the ampoule fits snugly in the tube and the gas generating solid material is between the tube open end and the ampoule.

13. A package according to claim 12 in which the means which prevents liquid flow is an absorbent plug located in the tube between the ampoule and the opening in the tube.

14. A package according to claim 12 in which a desiccant is positioned between the ampoule and the opening in the tube.

15. A package according to claim 2 in which the color indicator comprises:
   a container which permits flow of gas thereto,
   an ampoule in the container, said ampoule containing a redox color indicator liquid, and
   an absorbent material, for the liquid in the ampoule, in the container.

16. A package according to claim 15 in which the redox color indicator is methylene blue or resazurin.

17. A package according to claim 15 in which the color indicator container is a tube open at both ends.

18. A package according to claim 17 in which the tube is made of a transparent flexible polymeric material.

19. A package according to claim 18 in which the ampoule containing the indicator liquid fits snugly in the tube and is rupturable by squeezing the tube.

20. A package according to claim 19 in which the absorbent material is a white plug which fits snugly in the tube.

21. A package according to claim 17 in which each end of the tube is covered by a gas permeable filter.

22. A package according to claim 17 in which each end of the tube has a cap with a hole for gas flow and the hole is covered by a filter.

23. A package for storing and transporting an anaerobic culture comprising:
   a bag of flexible sheet material of low gas permeability;
   a self-contained gas generating apparatus in the bag for generating at least a reducing gas;
   a culture retaining receptacle in the bag;
   a catalyst in the bag which promotes reaction between the reducing gas, when produced by the gas generating apparatus, and oxygen in the bag; and
   a color indicator apparatus in the bag which when activated indicates the presence or absence of oxygen in the bag by color change;
   said color indicator comprising a container which permits flow of gas thereto, an ampoule in the container, said ampoule containing a redox color indicator liquid, and an absorbent material, for the liquid in the ampoule, in the container.

24. A package according to claim 23 in which the redox color indicator is methylene blue or resazurin.

25. A package according to claim 23 in which the color indicator container is a tube open at both ends.

26. A package according to claim 25 in which the tube is made of a transparent flexible polymeric material.

27. A package according to claim 26 in which the ampoule fits snugly in the tube and is rupturable by squeezing the tube.

28. A package according to claim 27 in which the absorbent material is a white plug which fits snugly in the tube.

29. A package according to claim 25 in which each end of the tube is covered by a gas permeable filter.

30. A package according to claim 25 in which each end of the tube has a cap with a hole for gas flow and the hole is covered by a filter.

31. A package for use in storing and transporting an anaerobic culture comprising:
   a bag of flexible sheet material of low gas permeability;
   a self-contained gas generating apparatus in the bag for generating at least a reducing gas;
   a catalyst inside of the bag which promotes reaction between the reducing gas, when produced by the gas generator apparatus, and oxygen in the bag;
   a color indicator apparatus which when activated indicates the presence or absence of oxygen in the bag by color change; and
   the gas generating apparatus comprising:
   a container having an opening,
   a reducing gas generating solid material in the container,
   an ampoule containing a liquid which is reactive with the solid material to produce a reducing gas catalytically reactive with oxygen at room temperature, said ampoule being openable from outside the container to free the liquid to contact the solid material, and
   means in the container which prevents liquid from flowing from the container after the ampoule is opened but which permits flow of reducing gas generated in the container out of the opening.

32. A package for use in storing and transporting an anaerobic culture comprising:
   a bag of flexible sheet material of low gas permeability;
   a self-contained gas generating apparatus in the bag for generating at least a reducing gas;
   a catalyst inside of the bag which promotes reaction between the reducing gas, when produced by the gas generator apparatus, and oxygen in the bag;
   a color indicator apparatus which when activated indicates the presence or absence of oxygen in the bag by color change; and
   the color indicator comprising:
   an open container which permits flow of gas therethrough,
   an ampoule in the container, said ampoule containing a redox color indicator liquid, and
   an absorbent material, for the liquid in the ampoule, in the container.

33. A package according to claim 31 in which the gas generating apparatus has a solid desiccant material therein which absorbs water which may enter before the ampoule is opened, thereby preventing degradation or premature reaction of the gas generating solid material.

34. A package according to claim 31 in which the solid material in the gas generating apparatus produces hydrogen.

35. A package according to claim 34 in which the gas generating apparatus container contains a catalyst which induces reaction of the generated hydrogen with oxygen in the air to produce water.

* * * * *